(12) United States Patent
Tully

(10) Patent No.: US 6,309,598 B1
(45) Date of Patent: Oct. 30, 2001

(54) ELECTROCHEMICAL HEATER AND METHOD FOR STERILIZING

(76) Inventor: Thomas J. Tully, 3178 Victoria Ave., Cincinnati, OH (US) 45208

(*) Notice: Subject to any disclaimer, the term of this patent is extended or adjusted under 35 U.S.C. 154(b) by 0 days.

(21) Appl. No.: 09/500,097

(22) Filed: Feb. 8, 2000

(51) Int. Cl.$^7$ ........................................ A01N 1/00
(52) U.S. Cl. ................. 422/28; 422/26; 422/28; 422/171; 422/294; 126/263; 126/263.01; 126/263.02; 126/263.03; 126/263.04; 126/263.05
(58) Field of Search ................. 422/26, 28, 171, 422/294; 126/263, 263.01, 263.02, 263.05, 263.07

(56) References Cited

U.S. PATENT DOCUMENTS

| | | | |
|---|---|---|---|
| 3,326,747 | * 6/1967 | Ryan et al. | 167/17 |
| 3,774,589 | * 11/1973 | Kober | 126/263 |
| 3,851,654 | * 12/1974 | Kober | 132/33 |
| 3,903,011 | 9/1975 | Donnelly . | |
| 4,338,098 | * 7/1982 | Yamaji | 44/3 |
| 4,501,259 | 2/1985 | Apellaniz . | |
| 4,522,190 | * 6/1985 | Kuhn et al. | 126/263 |
| 5,117,809 | * 6/1992 | Scaringe et al. | 126/263 |
| 5,220,909 | 6/1993 | Pickard et al. . | |
| 5,248,486 | 9/1993 | Matsuoka et al. . | |
| 5,390,659 | 2/1995 | Scaringe et al. . | |
| 5,538,020 | * 7/1996 | Farrier et al. | 131/369 |
| 5,593,792 | 1/1997 | Farrier et al. . | |
| 5,611,329 | * 3/1997 | Lamensdorf | 126/263.01 |
| 5,809,786 | 9/1998 | Scudder et al. . | |
| 5,820,691 | 10/1998 | Hartman . | |
| 5,918,590 | * 7/1999 | Burkett et al. | 126/263.01 |
| 5,935,486 | * 8/1999 | Bell et al. | 126/263.01 |
| 5,975,074 | * 11/1999 | Koiso et al. | 126/263.02 |
| 5,984,995 | * 11/1999 | White | 126/263.05 |

OTHER PUBLICATIONS

Merriam Webster's Collegiate Dictionary Tenth Edition, 1998, p. 261.*

* cited by examiner

Primary Examiner—Robert J. Warden, Sr.
Assistant Examiner—Imad Soubra
(74) Attorney, Agent, or Firm—Steven J. Rosen

(57) ABSTRACT

An electrochemical heating pad includes a corrugated sheet having alternating peaks and valleys defining channels of elongated compartments having sidewalls between the peaks and valleys. A dry mixture operable to be wetted and activated with an electrolyte to generate heat through electrochemical reactions is disposed in at least some of and preferably all of the elongated compartments. The channels are covered with a base sheet on or a porous sheet to form the compartments. The corrugated sheet is preferably made from cardboard and the porous sheet is made from non-woven polypropelene. One dry mixture of the invention includes Magnesium in a range of 80% to 95% by weight, Iron in a range of 3% to 6% by weight, and Calcium Nitrate in a range of 1% to 2% by weight. Another mixture includes about 83.5% Magnesium by weight, about 4.0% Iron by weight, about 11.0% salt by weight, and about 1.5% Calcium Nitrate by weight. Another embodiment of the invention is a method of sterilizing one or more articles in the electrochemical heating module by placing articles to be sterilized, the storage container, and the pad in the tray, opening the storage container such that the activator liquid reacts exothermically with the pad; sealing the tray in the sealable container until the more articles are sterilized. Iodine may be included in the activator liquid or otherwise used in the reaction.

26 Claims, 5 Drawing Sheets

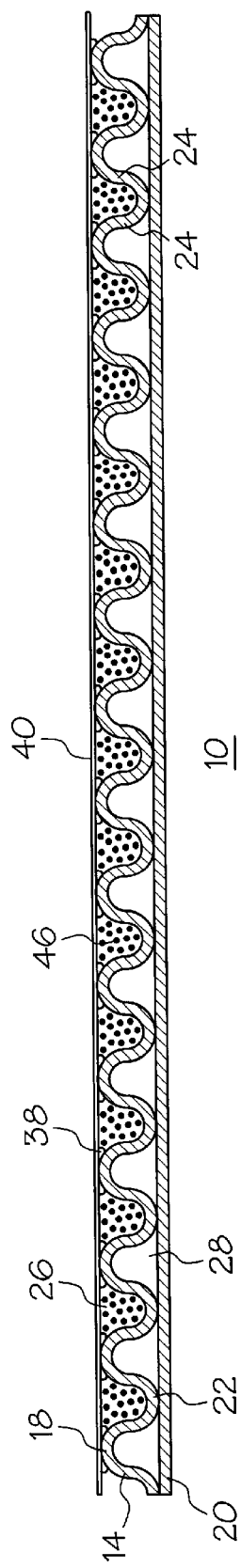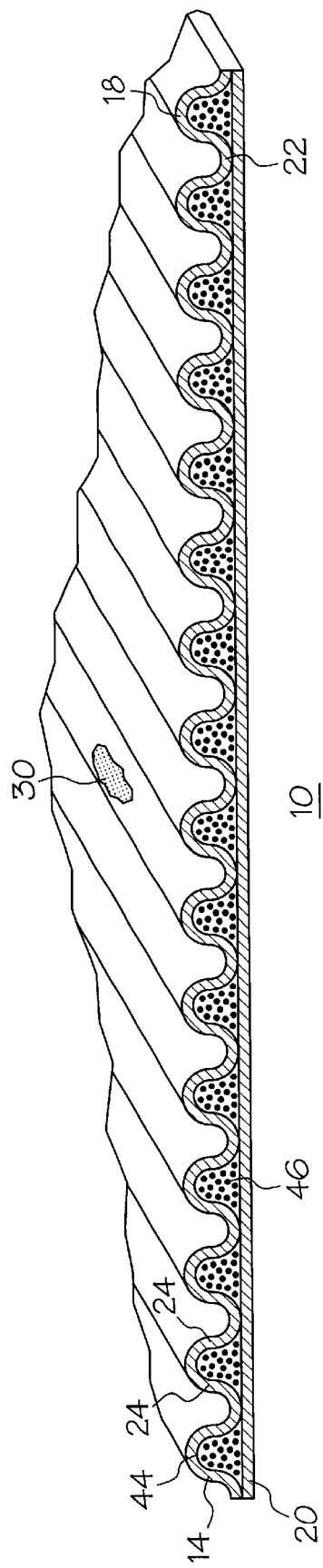

ELECTROCHEMICAL HEATER AND METHOD FOR STERILIZING

BACKGROUND OF THE INVENTION

1. Field of the Invention

The present invention relates to electrochemical heating and, more particularly, to an electrochemical heater pad and methods for using the pad particularly for sterilizing.

2. Description of Related Art

The manufacture of flameless heaters is well known in the art and used by, for example, the military as set forth in Military Specification MIL-R-44398A (Jul. 10, 1990) as disclosed in U.S. Pat. No. 5,117,809. A basic problem with present heater pads is the method for packaging them. The methods and the heater pads are costly and difficult to rapidly mass produce. A typical heater pad contains loose materials, typically in the form of powdered metals stored in a compartment and, which produce an exothermal reaction when water is added to the materials. The heater pad may be rigid with the powdered metals suspended in a plastic material.

It is desirable to provide a heater pad which holds the loose heater materials in place and provides an even distribution of the heat during the electrochemical exothermic reaction and a product with a specific heater mixture for production of the necessary heat, control of the heating rate and suppression of the hydrogen production, and which is easy to mass produce.

SUMMARY OF THE INVENTION

An electrochemical heating pad includes a corrugated sheet having alternating peaks and valleys defining channels of elongated compartments having sidewalls between the peaks and valleys. A dry mixture operable to be wetted and activated with an electrolyte or just water to generate heat through electrochemical reactions is disposed in at least some of and preferably all of the elongated compartments. The compartments may be formed from the channels covered with a base sheet on or a porous sheet that covers and seals the compartments. The porous sheet is preferably sealingly bonded to the corrugated sheet along the peaks.

In the exemplary embodiment of the invention, the corrugated sheet is made from cardboard and the porous sheet is made from non-woven polypropelene. The exemplary embodiment also includes the dry mixture having Magnesium in a range of 80% to 95% by weight, Iron in a range of 3% to 6% by weight, and Calcium Nitrate in a range of 1% to 2% by weight. A more particular embodiment includes the dry mixture having about 83.5% Magnesium by weight, about 4.0% Iron by weight, about 11.0% salt by weight, and about 1.5% Calcium Nitrate by weight. Another more particular embodiment includes the dry mixture having about 92.7% Magnesium by weight, about 5.5% Iron by weight, and about 1.8% Calcium Nitrate by weight.

Another embodiment of the electrochemical heating pad includes at least one compartment, a dry mixture operable to be wetted and activated with an electrolyte or water to generate heat through electrochemical reactions, and at least a portion of the compartment is made of a porous material. The mixture includes Magnesium in a range of 80% to 95% by weight, Iron in a range of 3% to 6% by weight, and Calcium Nitrate in a range of 1% to 2% by weight. A more particular embodiment includes the dry mixture having about 83.5% Magnesium by weight, about 4.0% Iron by weight, about 11.0% salt by weight, and about 1.5% Calcium Nitrate by weight. Another more particular embodiment includes the dry mixture having about 92.7% Magnesium by weight, about 5.5% Iron by weight, and about 1.8% Calcium Nitrate by weight. In place of Calcium Nitrate, the dry mixture may include other hydrogen suppressing oxidizing agents. The activator liquid may be just water if a salt is placed in the mixture. Alternatively, the activator liquid may be an electrolyte such as salt water.

Another embodiment of the present invention is an electrochemical heating module including an exothermic electrochemical heating pad, a tray for holding the heating pad and activator liquid including a germicide such as iodine, the activator liquid stored in a liquid storage container, and a sealable container for receiving the tray, heating pad, and activator liquid. In one embodiment, the electrochemical heating module includes the dry mixture of the present invention contained within the pad. Other antimicrobial or disinfecting agents may be used either in the activator liquid or mixed in with the dry mixture.

Another embodiment of the invention is a method of sterilizing one or more articles in the electrochemical heating module by placing the one or more articles to be sterilized, the storage container, and the pad in the tray, opening the storage container such that the activator liquid reacts exothermically with the pad and the disinfecting agent mixes with the activator liquid; sealing the tray in the sealable container until the one or more articles are sterilized.

The heater pad of the present invention is inexpensive and easy to mass produce. The compartments between the corrugations of the corrugated cardboard holds the loose exothermic materials in place during transportation during the reaction and provides an even distribution for a good complete exothermic reaction when liquid is added. The invention provides a heater pad which holds the loose heater materials in place and provides an even distribution of the heat during the electrochemical exothermic reaction and a product with a specific heater mixture for production of the necessary heat. The invention also controls of the heating rate and suppresses unwanted hydrogen production. The invention also provides apparatus and a method for sterilization such as for surgical instruments using a heater pad and module.

BRIEF DESCRIPTION OF THE DRAWINGS

The foregoing aspects and other features of the invention are explained in the following description, taken in connection with the accompanying drawings where:

FIG. 2 is cross-sectional view illustration of the heater pad taken through line 2—2 in FIG. 1.

DETAILED DESCRIPTION OF THE INVENTION

Figure 1:
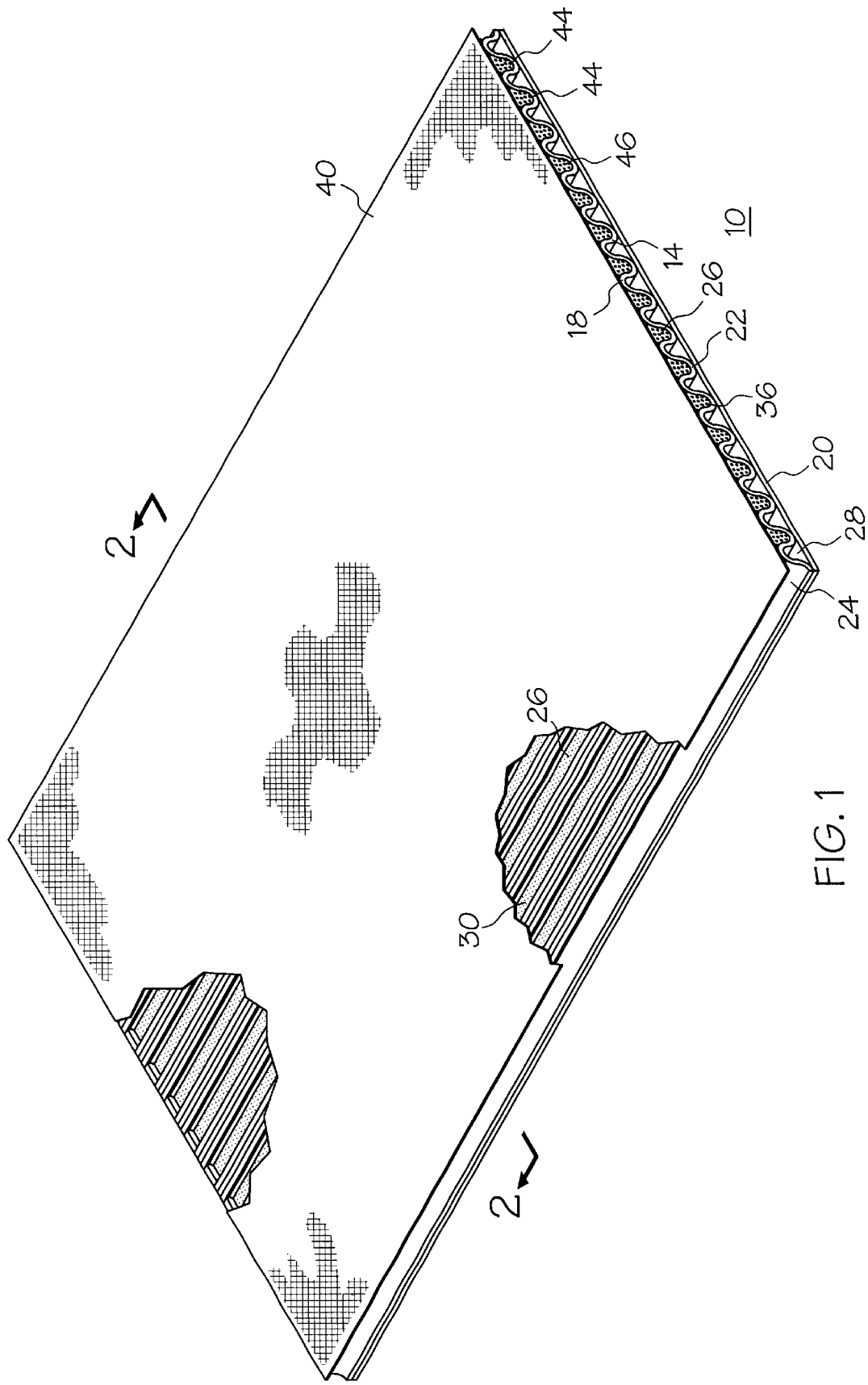
FIG. 1 is a schematic illustration of an exemplary embodiment of a heater pad of the present invention.

Illustrated in FIGS. 1 and 2 is an exemplary embodiment of the present invention, an electrochemical heating pad 10 having a corrugated sheet 14 having alternating peaks 18 and valleys 22 and sidewalls 24 between the peaks and valleys and with open channels 16 between the peaks. The corrugated sheet 14 preferably includes a flat base sheet 20 to which the corrugated sheet is attached forming elongated enclosed compartments 28 formed between the valleys 22 and bounded by flat base sheet. The electrochemical heating pad 10 includes a dry mixture 30 operable to be wetted and activated with an electrolyte 34 which is stored in a container such as a sealed plastic bag 50 illustrated in FIGS. 3–5 and which is operable to generate heat through electrochemical or exothermic reactions. The electrolyte 34 serves as an activator liquid and in one embodiment is salt water. Alternatively water may serve as the activator liquid if the a salt or some other electrolytic powder is placed in the mixture.

A first embodiment of the electrochemical heating pad 10 includes the mixture 30 disposed in at least some of and preferably all of the channels 16. The channels 16 are filled with the dry mixture 30 and a porous sheet 40 is attached to the corrugated sheet to cover and seal the open channels 16. The porous sheet 40 is sealingly bonded to the corrugated sheet 14 along the peaks 18 forming elongated sealed compartments 26 as illustrated in FIGS. 1 and 2. The porous sheet 40 may be bonded to the corrugated sheet 14 along the peaks 18 using glue or heat and pressure to form a bond 38. Illustrated in FIG. 2A is a second embodiment of the electrochemical heating pad 10 including the mixture 30 disposed in at least some of and preferably all of the enclosed compartments 28.

The open compartments 26 or the enclosed compartments 28, depending on which are filled, are sealed at compartment ends 44 with a sealant 46, or alternative sealing means such as crimping or bonding, forming sealed ends of the open compartments 26 and/or the enclosed compartment 28 embodiment of the invention, the corrugated sheet 14 is made from cardboard and the porous sheet 40 is made from non-woven polypropelene. The electrochemical heating pad 10 may also be constructed with both the sealed compartments 26 and the enclosed compartments 28 filled with the mixture 30 and sealed at the compartment ends 44 with the sealant 46.

In the exemplary embodiment, the dry mixture includes Magnesium in a range of 80% to 95% by weight, Iron in a range of 3% to 6% by weight, and Calcium Nitrate in a range of 1% to 2% by weight. The Calcium Nitrate is used as a means for suppressing Hydrogen production. In place of Calcium Nitrate, the dry mixture may include other hydrogen suppressing oxidizing agents such as Calcium Hydroxide, Sodium Chloride (salt which is thought to be mildly effective), Sodium Nitrate, Sodium Nitrite, Iodates (salts of iodic acid which is a powerful oxidizing agent), and Potassium Permanganate.

In a more particular embodiment, the dry mixture includes about 83.5% Magnesium by weight, about 4.0% Iron by weight, about 11.0% salt by weight, and about 1.5% Calcium Nitrate by weight. In another more particular embodiment, the dry mixture includes about 92.7% Magnesium by weight, about 5.5% Iron by weight, and about 1.8% Calcium Nitrate by weight.

Other types of compartments may be used for the electrochemical heating pad so long as it includes at least one compartment, a dry mixture operable to be wetted and activated with an electrolyte to generate heat through electrochemical reactions, and at least a portion of the compartment is made of a porous material. The mixture includes Magnesium in a range of 80% to 95% by weight, Iron in a range of 3% to 6% by weight, and Calcium Nitrate in a range of 1% to 2% by weight.

Figure 3:
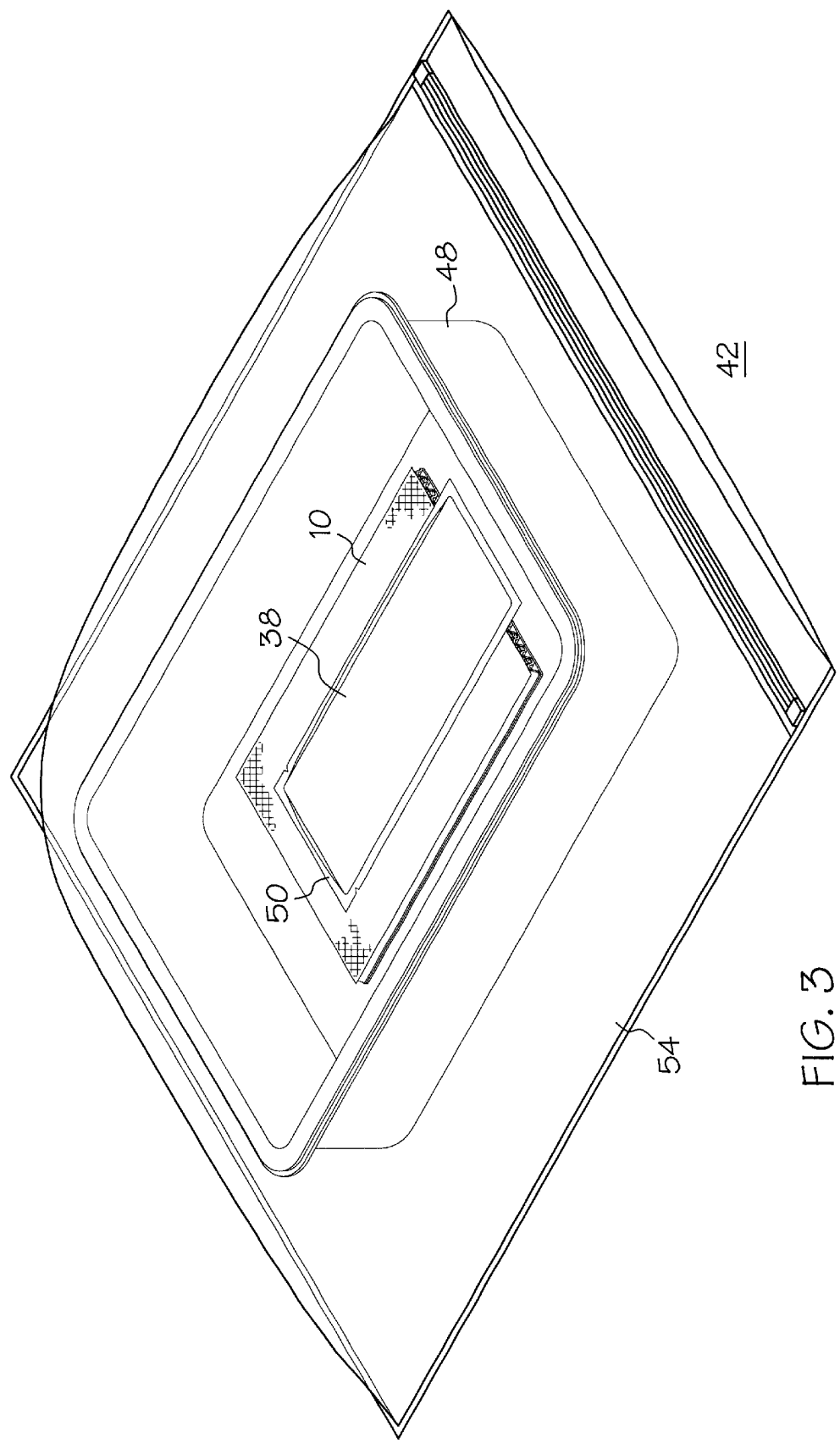
FIG. 3 is a perspective view illustration of a heater kit having the heater pad in FIG. 1.
Figure 4:
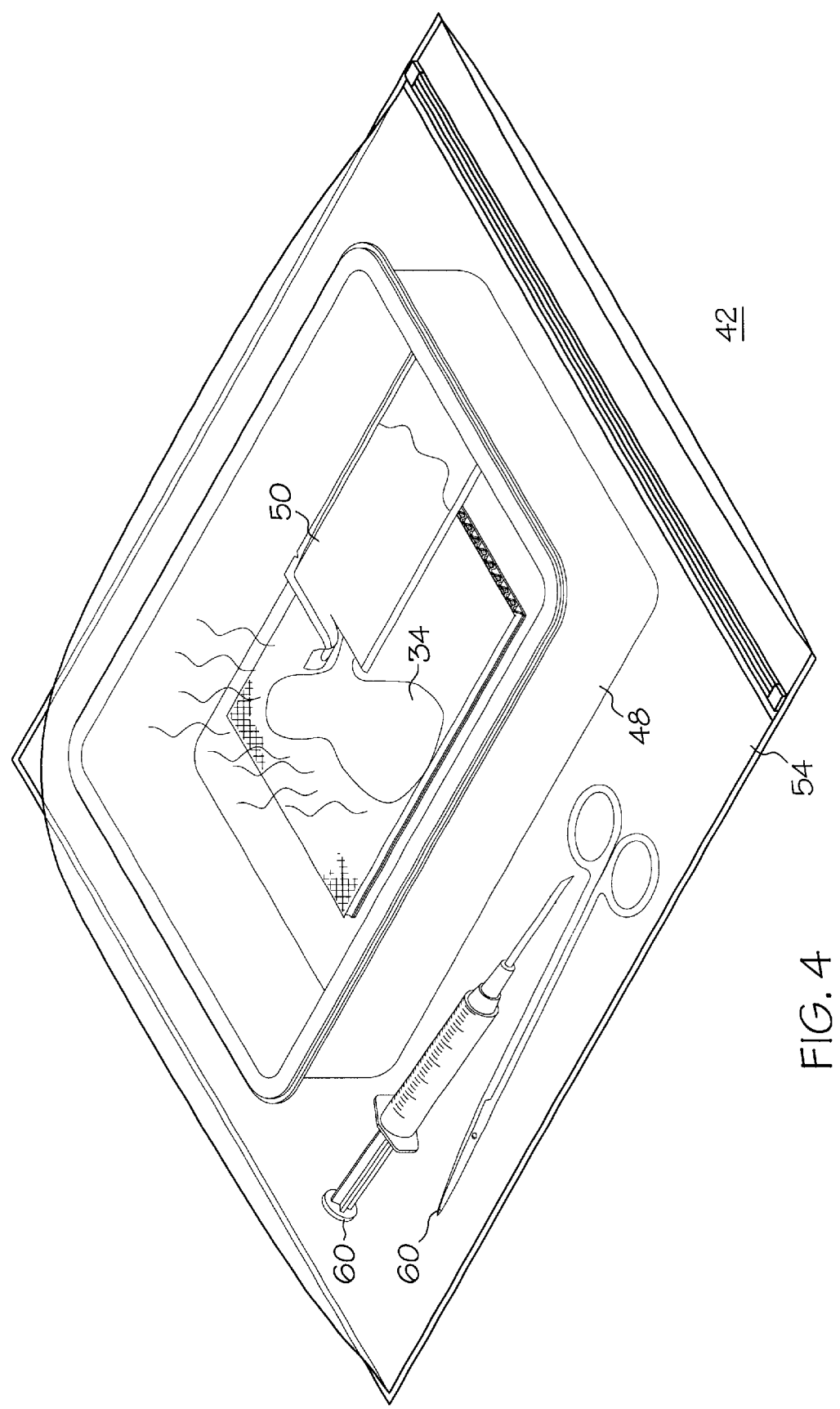
FIG. 4 is a perspective view illustration of the heater kit in FIG. 1 used to heat a food container.

A more particular embodiment of the present invention is an electrochemical heating module 42 including the exothermic electrochemical heating pad 10, a tray 48 for holding the heating pad and activator liquid (such as the electrolyte 34) stored in a container in the form of a sealed plastic bag 50 as illustrated in FIG. 3. The tray 48 holds the heating pad 10 and the activator liquid stored in the sealed plastic bag 50, all of which comes with a sealable container illustrated as a sealable plastic bag 54. The object to be heated, such an instant soup in a food container 52, is placed in the tray 48 as illustrated in FIG. 4 on top of the heating pad 10. The activator liquid stored is released from the sealed plastic bag 50 by tearing or puncturing the sealed plastic bag in the tray 48. Then the activator liquid seeps through the electrochemical heating pad 10 into the sealed compartments 26 or the enclosed compartments 28, depending on which embodiment of the heating pad 10 is being used, and wets the dry mixture 30 which generates heat through electrochemical exothermic reactions. The activator liquid seeps into the compartments through the porous sheet 40 and/or through the corrugated sheet 14 if it is made from cardboard or some other porous material such as the non-woven polypropelene. One or more vent holes (not illustrated) in the sealable plastic bag 54 may be used to vent steam and other vapors generated by the electrochemical exothermic reactions.

Figure 5:
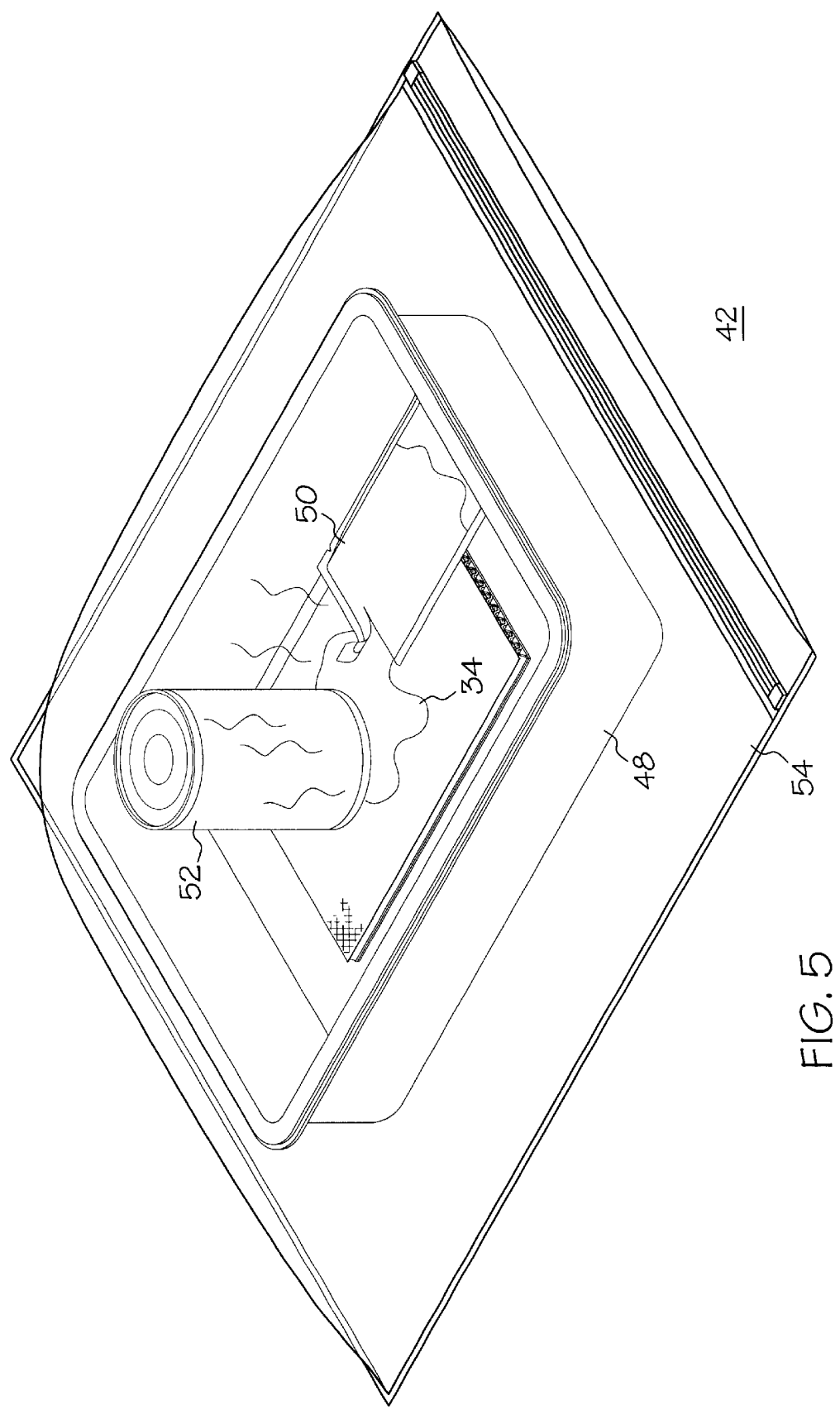
FIG. 5 is a perspective view illustration of the heater kit in FIG. 1 used to sanitize surgical instruments.

Illustrated in FIG. 5, is another embodiment of the invention that is used for sterilizing objects such as surgical instruments 60. Iodine is added to the mixture or the activator liquid that is stored in a liquid storage container such as the sealed plastic bag 50. This helps sterilize the objects placed in the sealable container in addition to the heat generated through the electrochemical exothermic reactions. A sealable container such as the sealable bag is also preferably used for receiving the tray, heating pad, and activator liquid as well as the surgical instruments or other objects to be sterilized. In some applications, sterilization may also be accomplished without the use of iodine. The iodine in the activator liquid serves as a disinfecting agent. The disinfecting agents may be used in the activator liquid or, alternatively, mixed in with the dry mixture. Suitable disinfecting agents include antimicrobial agents, Benzoic Acid, Iodine Tincture, Phenylboric Acid, Sodium Chloride (mildly effective), Sodium Nitrate, Phenylboric Acid, Sodium Nitrate, Iodinate compounds, Iodates (salts of iodic acid), and Potassium Permanganate.

Another embodiment of the invention is a method of sterilizing one or more articles in the electrochemical heating module by placing the one or more articles to be sterilized, the storage container, and the pad in the tray, opening the storage container such that the activator liquid reacts exothermically with the pad; sealing the tray in the sealable container until the one or more articles are sterilized.

While the preferred embodiment of the present invention has been described fully in order to explain its principles, it is understood that various modifications or alterations may be made to the preferred embodiment without departing from the scope of the invention as set forth in the appended claims.

What is claimed is:

1. An electrochemical heating pad, said pad comprising:
   a cardboard corrugated sheet having alternating peaks and valleys,
   elongated compartments between said peaks and between said valleys and having sidewalls between said peaks and valleys, a dry mixture operable to be wetted and activated with an activating liquid to generate heat through electrochemical reactions, said mixture disposed in at least some of said elongated compartments, said elongated compartments comprising;

open channels between said peaks, said mixture disposed in at least some of said channels, and said channels covered and sealed with a porous sheet sealingly bonded to said corrugated sheet along said peaks.

2. An electrochemical heating pad, said pad comprising:

a cardboard corrugated sheet having alternating peaks and valleys, elongated compartments between said peaks and between said valleys and having sidewalls between said peaks and valleys, a dry mixture operable to be wetted and activated with an activating liquid to generate heat through electrochemical reactions, said mixture disposed in at least some of said elongated compartments, said cardboard corrugated sheet further comprising a base sheet attached to said valleys and said elongated compartments comprise enclosed channels between said peaks and between said valleys and said base sheet and said mixture disposed in at least some of said enclosed compartments.

3. An electrochemical heating pad as claimed in claim 1 wherein said porous sheet is made from non-woven polypropelene.

4. An electrochemical heating pad, said pad comprising:

a cardboard corrugated sheet having alternating peaks and valleys, elongated compartments between said peaks and between said valleys and having sidewalls between said peaks and valleys, a dry mixture operable to be wetted and activated with an activating liquid to generate heat through electrochemical reactions, said mixture disposed in at least some of said elongated compartments, said dry mixture comprising Magnesium in a range of 80% to 95% by weight, Iron in a range of 3% to 6% by weight, and Calcium Nitrate in a range of 1% to 2% by weight.

5. An electrochemical heating pad, said pad comprising:

a cardboard corrugated sheet having alternating peaks and valleys, elongated compartments between said peaks and between said valleys and having sidewalls between said peaks and valleys, a dry mixture operable to be wetted and activated with an activating liquid to generate heat through electrochemical reactions, said mixture disposed in at least some of said elongated compartments, said dry mixture comprising about 83.5% Magnesium by weight, about 4.0% Iron by weight, about 11.0% Salt by weight, and about 1.5% Calcium Nitrate by weight.

6. An electrochemical heating pad, said pad comprising:

a cardboard corrugated sheet having alternating peaks and valleys, elongated compartments between said peaks and between said valleys and having sidewalls between said peaks and valleys, a dry mixture operable to be wetted and activated with an activating liquid to generate heat through electrochemical reactions, said mixture disposed in at least some of said elongated compartments, said dry mixture comprising about 92.7% Magnesium by weight, about 5.5% Iron by weight, and about 1.8% Calcium Nitrate by weight.

7. An electrochemical heating pad as claimed in claims 4, 5, or 6 wherein said corrugated sheet is made from cardboard.

8. An electrochemical heating pad as claimed in claim 6 wherein said porous sheet is made from non-woven polypropelene.

9. An electrochemical heating pad, said pad comprising:

at least one compartment, a dry mixture operable to be wetted and activated with an activating liquid to generate heat through electrochemical reactions, said mixture disposed in said compartment, said dry mixture comprising Magnesium in a range of 80% to 95% by weight, Iron in a range of 3% to 6% by weight, and Calcium Nitrate in a range of 1% to 2% by weight, and at least a portion of said compartment made of a porous material.

10. An electrochemical heating pad as claimed in claim 9 wherein said dry mixture comprises about 83.5% Magnesium by weight, about 4.0% Iron by weight, about 11.0% Salt by weight, and about 1.5% Calcium Nitrate by weight.

11. An electrochemical heating pad as claimed in claim 9 wherein said dry mixture comprises about 92.7% Magnesium by weight, about 5.5% Iron by weight, and about 1.8% Calcium Nitrate by weight.

12. An electrochemical heating module comprising:

an exothermic electrochemical heating pad, a tray for holding said heating pad and an activator liquid stored in a liquid storage container, and a sealable container for receiving said tray, heating pad, and activator liquid, a disinfecting agent suitably stored to be mixed with said activator liquid and said pad.

13. An electrochemical heating module as claimed in claim 12 further comprising a dry mixture contained within said pad, said dry mixture comprises Magnesium in a range of 80% to 95% by weight, Iron in a range of 3% to 6% by weight, and Calcium Nitrate in a range of 1% to 2% by weight.

14. An electrochemical heating module as claimed in claim 13 wherein said dry mixture comprises about 83.5% Magnesium by weight, about 4.0% Iron by weight, about 11.0% Salt by weight, and about 1.5% Calcium Nitrate by weight.

15. An electrochemical heating module as claimed in claim 13 wherein said dry mixture comprises about 92.7% Magnesium by weight, about 5.5% Iron by weight, and about 1.8% Calcium Nitrate by weight.

16. An electrochemical heating module as claimed in claim 15 wherein said corrugated sheet is made from cardboard.

17. An electrochemical heating module as claimed in claim 16 wherein said porous sheet is made from non-woven polypropelene.

18. An electrochemical heating module as claimed in claims 13, 14, or 15 wherein said pad comprises:

a corrugated sheet having alternating peaks and valleys defining sidewalls of open elongated compartments between said peaks, said mixture disposed in at least some of said open elongated compartments, and a porous sheet covering and sealing said compartments and sealingly bonded to said corrugated sheet along said peaks.

19. An electrochemical heating module as claimed in claim 18 wherein said disinfecting agent is iodine in said liquid.

20. A method of sterilizing one or more articles in an electrochemical heating module including an exothermic electrochemical heating pad, a tray for holding the heating pad and a storage container containing activator liquid, a disinfecting agent suitably stored to be mixed with said activator liquid, and a sealable container for receiving the tray, heating pad, disinfecting agent, and activator liquid, said method comprising:

placing the one or more articles, the storage container, and the pad in the tray, opening the storage container such that the activator liquid reacts exothermically with the pad and mixes with the disinfecting agent;

sealing the tray in the sealable container until the one or more articles are sterilized.

21. A method as claimed in claim 20 wherein the pad comprises a dry mixture contained within the pad and the dry mixture comprises Magnesium in a range of 80% to 95% by weight, Iron in a range of 3% to 6% by weight, and Calcium Nitrate in a range of 1% to 2% by weight.

22. A method as claimed in claim 20 wherein the dry mixture comprises about 83.5% Magnesium by weight, about 4.0% Iron by weight, about 11.0% Salt by weight, and about 1.5% Calcium Nitrate by weight.

23. A method as claimed in claim 20 wherein the dry mixture comprises about 92.7% Magnesium by weight, about 5.5% Iron by weight, and about 1.8% Calcium Nitrate by weight.

24. A method as claimed in claims 21, 22, or 23 wherein the pad comprises:

a corrugated sheet having alternating peaks and valleys defining sidewalls of elongated compartments between the peaks, the mixture is disposed in at least some of the elongated compartments, and a porous sheet covering and sealing the compartments and sealingly bonded to the corrugated sheet along the peaks.

25. A method as claimed in claim 24 wherein the corrugated sheet is made from cardboard.

26. A method as claimed in claim 25 wherein the disinfecting agent is iodine in the activator liquid.

* * * * *